(12) United States Patent
Yu et al.

(10) Patent No.: US 8,722,388 B2
(45) Date of Patent: May 13, 2014

(54) VECTOR AND MICROORGANISM FOR INCREASING GALACTOSE CATABOLISM AND METHODS THEREFOR

(75) Inventors: Byung Jo Yu, Hwaseong-si (KR); Jae Chan Park, Yongin-si (KR); Hyun Min Koo, Seoul (KR); Yong Su Jin, Suwon-si (KR); Ki Sung Lee, Suwon-si (KR)

(73) Assignee: Samsung Electronics Co. Ltd., Suwon-Si (KR)

( * ) Notice: Subject to any disclaimer, the term of this patent is extended or adjusted under 35 U.S.C. 154(b) by 486 days.

(21) Appl. No.: 12/481,193

(22) Filed: Jun. 9, 2009

(65) Prior Publication Data

US 2010/0105573 A1    Apr. 29, 2010

(30) Foreign Application Priority Data

Oct. 29, 2008    (KR) .................. 10-2008-0106278

(51) Int. Cl.
*C12N 1/00* (2006.01)
*C12N 1/19* (2006.01)

(52) U.S. Cl.
USPC .................................... 435/255.1; 435/254.2

(58) Field of Classification Search
None
See application file for complete search history.

(56) References Cited

U.S. PATENT DOCUMENTS

| 7,393,669 | B2 | 7/2008 | Bro et al. |
| 2005/0009135 | A1 | 1/2005 | Bro et al. |
| 2009/0307788 | A1* | 12/2009 | Nielsen ........................... 800/13 |

FOREIGN PATENT DOCUMENTS

| WO | 2005121337 A1 | 12/2005 |
| WO | 2007147409 A2 | 12/2007 |
| WO | 2008105618 A1 | 9/2008 |

OTHER PUBLICATIONS

Burgers et al. Structure and processivity of two forms of *Saccharomyces cerevisiae* DNA polymerase delta. J Biol Chem. Jul. 31, 1998;273(31):19756-62.*
Sikorski et al. A system of shuttle vectors and yeast host strains designed for efficient manipulation of DNA in *Saccharomyces cerevisiae*. Genetics. May 1989;122(1):19-27.*
Campbell. Biology. 3d. The Benjamin /Cummings Publishing Co., Inc., 1993, pp. 399, 592.*
Lee et al. Improved galactose fermentation of *Saccharomyces cerevisiae* through inverse metabolic engineering. Biotechnol Bioeng. Mar. 2011;108(3):621-31.*
Bro, C. et al., Improvement of Galactose Uptake in *Saccharomyces cerevisiae* through Overexpression of Phosphoglucomutase: Example of Transcript Analysis as a Tool in Inverse Metabolic Engineering, Applied and Environmental Microbiology, 2005, vol. 71, No. 11, pp. 6465-6472.
Ostergaard, S. et al., Increasing galactose consumption by *Saccharomyces cerevisiae* through metabolic engineering of the GAL gene regulatory network, Nature Biotechnology, 2000, 18: pp. 1283-1286.
Ostergaard, S. et al., The impact of GAL6, GAL80, and MIG1 on glucose control of the GAL system in *Saccharomyces cerevisiae*, FEMS yeast research, 2001,1(1):47-55.
EBI accession No. EMBL: u03453, yeast episomal vector pRS424 with TRP1 marker (Nov. 17, 1993). (XP0025635950).
EBI accession No. EMBL: AY253285, *Saccharomyces cerevisiae* non-coding RNA RUF1 (last updated Mar. 31, 2004). (XP002563593).
EBI accession No. GSN: AOG46773, *Saccharomyces cerevisiae* SNR84 sequence, SEQ ID No. 846 of WO2007147409 (Mar. 6, 2008). (XP00256392).
Christianson T.W. et al., Multifunctional yeast high-copy-number shuttle vectors, Gene. 1992; 110:119-122.
McCutcheon J.P. et al., Computational identification of non-coding RNAs in *Saccharomyces cerevisiae* by comparative genomics, Nucleic Acids Res. 2003; 31(14): 4119-4128.
Keating, J. D. et al., Characterization of a unique ethanologenic yeast capable of fermenting galactose, Enzyme and Microbial Technology, 2004; 35: 242-253.
European Extended Search Report for Application No. 09172015.1 dated Feb. 8, 2010.
*Saccharomyces cerevisiae* non-coding RNA RUF1; GenBank Acc. No. AY253285. [online]. Mar. 30, 2004. NCBI.
*Saccharomyces cerevisiae* chromosome IV, complete sequence, NC_001136 REGION: 1492241.. 194948. Oct. 30, 2013.
Jin et al., "Improvement of Xylose Uptake and Ethanol Production in Recombinant *Saccharomyces cerevsiae* through an Inverse Metabolic Engineering Approach," *Appl. Environ. Microbiol.*, 71(12), 8249-8259 (2005).

* cited by examiner

*Primary Examiner* — Michele K Joike
(74) *Attorney, Agent, or Firm* — Leydig, Voit & Mayer, Ltd.

(57) ABSTRACT

Provided herein are a recombinant vector and microorganism including the isolated SNR84 gene, and a method of increasing volumetric productivity of biofuel from a galactose-containing carbon source using the isolated SNR84 gene, the recombinant vector or the recombinant microorganism. Also disclosed herein is a method of screening yeast for genes associated with increased galactose catabolism when the genes are overexpressed.

9 Claims, 5 Drawing Sheets

SEQUENCE LISTING

```
<160> NUMBER OF SEQ ID NOS: 1

<210> SEQ ID NO 1
<211> LENGTH: 550
<212> TYPE: DNA
<213> ORGANISM: Saccharomyces cerevisiae
<220> FEATURE:
<223> OTHER INFORMATION: snr gene

<400> SEQUENCE: 1
attgcacaac ttaagtttgt cgaggatcat tttttgaac tgaatcatgc tcttttaag      60 tgctttgaaa ccctcgatga atgtgtcaat gtgcaaagat aaaccattgt tctctgttga     120
tcagtgactt aatgtttgct ttggagaatg atattttccc tttcctatat ttgacttttg     180
ttctaaaagt tatttggaga gaaaaggcat gattgaggtt gcgacttttt cgtttttgct     240
tttgcatgga taattcatcc atgcacatct cactttattg gaccttcaag attggtttcc     300
catgtaattt aattttctct cctctacatt taatatgttc tatattaatt aataccaatt     360
gagttgtgcg tacttcattg cagatatttt accagacctg tctgagtttt tcgttcaagt     420
ttggttgaaa tcggcttgag gtatatgaac gtggttggga tatggagatt gggagatcaa     480
agaagcgaaa atacctgaga cagttttttt aaaaaagaag ctaaggaaca tgactcaaag     540
agacacatta                                                            550
```

VECTOR AND MICROORGANISM FOR INCREASING GALACTOSE CATABOLISM AND METHODS THEREFOR

CROSS-REFERENCE TO RELATED APPLICATION

This application claims priority to Korean Patent Application No. 10-2008-0106278, filed on Oct. 29, 2008, which is hereby incorporated by reference in its entirety.

BACKGROUND

1. Field

Exemplary embodiments relate to a gene associated with increased galactose catabolism, and to a recombinant vector and microorganism containing the same. More particularly, the overexpression of the SNR84 gene is associated with increased galactose catabolism.

2. Description of the Related Art

With globally increasing concern about the exhaustion of resources and pollution of the environment by overuse of fossil fuels, the development of new and renewable alternative energies sources that stably and continuously produce energy are being considered. In the ongoing developments of such alternative energy resources, technology for producing energy from biomass has been receiving considerable attention.

In recent times, there has been considerable interest around the prospect of using algae as a source of biomass. An advantage of using algae is its abundance and rapid growth. Also, since algae consume carbon dioxide and exhaust oxygen for growth, they offer a potential solution to both energy production and pollution concerns. However, algae have not yet been produced on a large scale and used in a variety of applications.

Hydrolysates of biomass derived from red algae contain a large amount of galactose. Accordingly, the effective use of galactose abundant in the hydrolysates is the first step toward developing a biological process for converting the biomass hydrolysates derived from algae into useful materials, using yeast or other fermenting microorganisms.

However, while galactose can be catabolized by yeast present in nature, its uptake and metabolic rate is much lower than that of glucose.

SUMMARY

In one embodiment, a gene for increasing galactose catabolism when overexpressed is provided, as well as a method of increasing the volumetric productivity of biofuel from a carbon source containing galactose by fermentation with yeast transformed with the gene. The gene associated with increased galactose catabolism is the SNR84 gene.

In another embodiment, a systematic biotechnological technique is provided for identifying genes associated with increased galactose catabolism on the genomic level.

According to another embodiment, a recombinant vector containing the gene for increasing galactose catabolism when overexpressed is provided. In some embodiments, the gene is the SNR84 gene.

The vector may be a plasmid, for example, plasmid pRS424.

According to another embodiment, a recombinant microorganism transformed with the recombinant vector containing the gene for increasing galactose catabolism when overexpressed is provided. The gene can be the SNR84 gene.

The recombinant microorganism may be yeast, which may be selected from the group consisting of the genus *Saccharomyces*, the genus *Pachysolen*, the genus *Clavispora*, the genus *Kluyveromyces*, the genus *Debaryomyces*, the genus *Schwanniomyces*, the genus *Candida*, the genus *Pichia*, and the genus *Dekkera*.

In one embodiment, the recombinant microorganism is *Saccharomyces cerevisiae* strain CEN.PK2-1D/pRS424-SNR84 deposited with the Korean Tissue Collection for Type Cultures with Accession No. KCTC 11388 BP.

According to another embodiment, a method of producing biofuel from a galactose-containing carbon source using a recombinant microorganism is provided. In one embodiment the method comprises transforming yeast with a recombinant vector comprising an isolated SNR84 gene to prepare a recombinant yeast strain, culturing the recombinant yeast strain in the galactose-containing carbon source, and overexpressing the SNR84 gene. The galactose-containing carbon source used to culture the yeast strain contains galactose, or a mixture of glucose and galatose.

In another embodiment, the method comprises culturing a recombinant microorganism comprising a gene which increases galactose catabolism when overexpressed in a galactose-containing medium under conditions such that a biofuel is produced by fermentation.

As disclosed herein, overexpression of the SNR84 gene leads to an increase in the volumetric productivity of a biofuel.

According to another embodiment, a method of screening a yeast gene, which increases galactose catabolism when the gene overexpressed, is provided. The method includes: constructing a yeast genomic DNA library using a multi-copy plasmid containing a trp promoter; transforming a yeast with the constructed genomic DNA library, preparing a library of the transformed yeast in which yeast genes inserted in the multi-copy plasmid are overexpressed; culturing the transformed yeast library in a medium containing only galactose as a carbon source; screening the transformed yeast for colonies having increased galactose catabolism, wherein the screening comprises identifying fast-growing colonies through serial subculture; isolating the plasmid from the screened transformed yeast; and identifying a yeast genomic sequence inserted in the isolated plasmid.

As disclosed herein, the yeast may be *Saccharomyces cerevisiae* strain CEN.PK2-1D, and the multi-copy plasmid may be pRS424.

The method may further include: determining a location of the identified yeast genomic sequence on the yeast genome by comparing a base sequence of the yeast genome with a pre-determined length of genomic sequence present at each end of the insert gene in the plasmid to identify the overexpressed gene; re-transforming the yeast with a plasmid having the identified gene to confirm that an increase in galactose catabolism is caused by overexpression of the gene; or both processes described above.

BRIEF DESCRIPTION OF THE DRAWINGS

Exemplary embodiments are described in further detail below with reference to the accompanying drawings. It should be understood that various aspects of the drawings may have been exaggerated for clarity.

DETAILED DESCRIPTION

Figure 1:
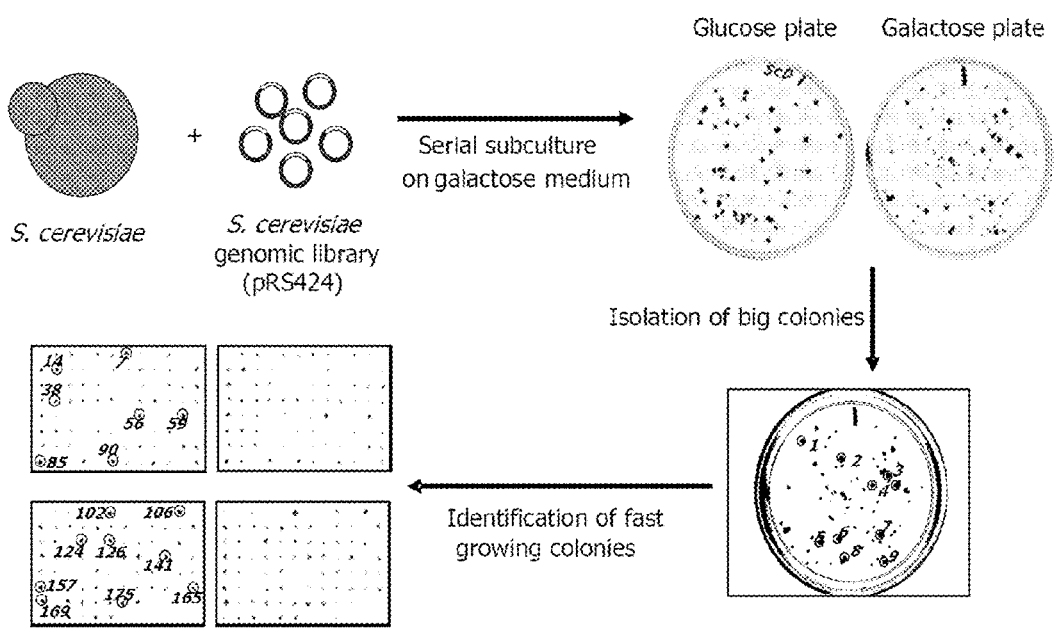
FIG. 1 is an illustration showing a method of screening genes according to an exemplary embodiment.

Hereinafter, the inventive concept will be described more fully with reference to exemplary embodiments and the accompanying drawings. However, it should be understood that the inventive concept is not limited to the described exemplary embodiments and may be embodied in various modifications and changes.

1. SNR84 Gene, Recombinant Vector, and Recombinant Microorganism

In one exemplary embodiment, a gene for increasing galactose catabolism when the gene is overexpressed is provided. In some embodiments the gene is the yeast SNR84 gene. The SNR84 gene may have a polynucleotide sequence set forth in SEQ.ID.NO: 1.

The SNR84 gene encodes H/ACA snoRNA (small nucleolar RNA), which is known to be involved in base modification, such as pseudouridylation, of the large subunit rRNA. The inventors have discovered that yeast that overexpress SNR84 exhibit significantly increased galactose catabolism.

Without being bound by theory, it is presumed that the function of the SNR84 gene involved in the pseudouridylation of large subunit rRNA is activated, which results in an improved maturation rate and quantity of large subunit rRNA produced. When mature large subunit rRNA is formed rapidly in an initial exponential phase, the production rate of most enzymes becomes higher. Thus, enzymes involved in galactose catabolism, as well as related enzymes, are expected to be rapidly produced on a large scale.

Galactose is an aldohexose with molecular formula $C_6H_{12}O_6$. Galactose is converted by many organisms, including yeast, first into galactose-1-phosphate and then into glucose-1-phosphate. In yeast and other microorganisms, the glucose-1-phosphate can subsequently be catabolized into alcohol by fermentation. In the galactose catabolic pathway, the alcohol production concentration per galactose consumption time is denoted as the volumetric productivity of the alcohol. Thus, an increase in galactose catabolism may also be expressed as an increase in the volumetric productivity of alcohol.

Galactose-catabolizing genes, i.e., genes involved in galactose uptake and metabolism, may include gal2, gal1, gal7, gal10, and gal5 (pgm1 or pgm2), but are not limited thereto.

The term 'galactose catabolism' refers to the metabolic degradation of galactose. The level of galactose catabolism is often expressed as the 'galactose utilization rate'.

In one embodiment, the SNR84 gene has the nucleotide sequence set forth in SEQ ID NO:1, or a nucleotide sequence having at least 60%, or at least 85%, or at least 95% sequence homology with the nucleotide sequence of SEQ ID NO:1 and having substantially the same function as the unmodified nucleotide sequence. The modified sequence may be obtained by deletion, substitution or addition of at least one base.

In another exemplary embodiment, a recombinant vector comprising an isolated polynucleotide encoding yeast SNR84 is provided.

The term "vector" refers to a nucleic acid molecule capable of transporting another nucleic acid to which it has been linked. Examples of vectors include bacteria, plasmids, phages, cosmids, episomes, viruses, and insertable DNA fragments (fragments able to be inserted into a host cell genome by homologous recombination), but are not limited thereto.

The term "plasmid" refers to circular, double-stranded DNA capable of inserting a foreign DNA fragment. Further, the term "virus vector" refers to a vector that may insert additional foreign DNA into a virus genome.

As used herein, when the vector directs the expression of a gene encoding a target protein or RNA operably connected thereto, the vector is called an "expression vector." Generally, in recombinant DNA technology, a plasmid is used as an expression vector, and thus the term "plasmid" may be interchangeably used with the term "expression vector." However, it should be clear that expression vectors also include other types of vectors exhibiting the same function, for example, a virus vector.

The expression vectors are able to be expressed and genetically recombined in yeast. Examples of expression vectors include vector II micron, pBM272, pBR322-6, pBR322-8, pCS19, pDW227, pDW229, pDW232, pEMBLYe23, pEMBLYe24, pEMBLYi21, pEMBLYi22, pEMBLYi32, pEMBLYr25, pFL2, pFL26, pFL34, pFL35, pFL36, pFL38, pFL39, pFL40, pFL44L, pFL44S, pFL45L, pFL45S, pFL46L, pFL46S, pFL59, pFL59+, pFL64−, pFL64+, pG6, pG63, pGAD10, pGAD424, pGBT9, pGK12, pJRD171, pKD1, pNKY2003, pNKY3, pNN414, pON163, pON3, pPM668, pRAJ275, pRS200, pRS303, pRS304, pRS305, pRS306, pRS313, pRS314, pRS315, pRS316, pRS403, pRS404, pRS405, pRS406, pRS413, pRS414, pRS415, pRS416, pRS423, pRS424, pRS425, pRS426, pRSS56, pSG424, pSKS104, pSKS105, pSKS106, pSZ62, pSZ62, pUC-URA3, pUT332, pYAC2, pYAC3, pYAC4, pYAC5, pYAC55, pYACneo, pYAC-RC, pYES2, pYESHisA, pYESHisB, pYESHisC, pYEUra3, rpSE937, YCp50, YCpGAL0, YCpGAL1, YCplac111, YCplac22, YCplac33, YDp-H, YDp-K, YDp-L, YDp-U, YDp-W, YEp13, YEp213, YEp24, YEp351, YEp352, YEp353, YEp354, YEp355, YEp356, YEp356R, YEp357, YEp357R, YEp358, YEp358R, YEplac112, YEplac181, YEplac195, YIp30, YIp31, YIp351, YIp352, YIp353, YIp354, YIp355, YIp356, YIp356R, YIp357, YIp357R, YIp358, YIp358R, YIp5, YIplac128, YIplac204, YIplac211, YRp12, YRp17, YRp7, pAL19, paR3, pBG1, pDBlet, pDB248X, pEA500, pFL20, pIRT2, pIRT2U, pIRT2-CAN1, pJK148, pJK210, pON163, pNPT/ADE1-3, pSP1, pSP2, pSP3, pSP4, pUR18, pUR19, pZA57, pWH5, pART1, pCHY21, pEVP11, REP1, REP3, REP4, REP41, REP42, REP81, REP82, RIP, REP3X, REP4X, REP41X, REP81X, REP42X, REP82X, RIP3X/s, RIP4X/s, pYZ1N, pYZ41N, pYZ81N, pSLF101, pSLF102, pSLF104, pSM1/2, p2UG, pART1/N795, and pYGT, but are not limited thereto.

Figure 4:
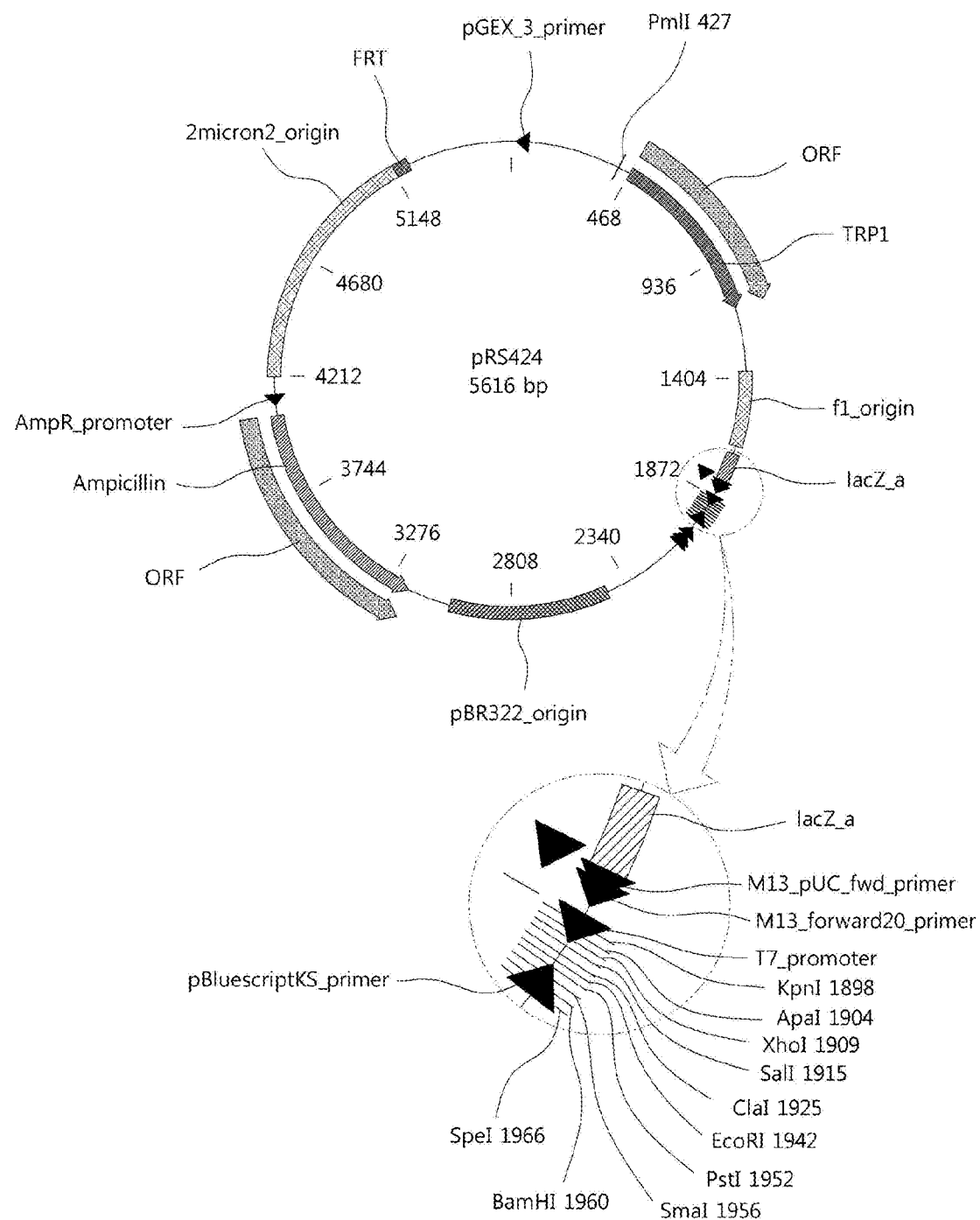
FIG. 4 is a map of plasmid pRS424.

In one example, the plasmid may be the expression vector pRS424 having the map shown in FIG. 4.

The expression vector may be introduced into a host cell by transformation, and therein produce an RNA, a protein or a peptide, or possibly a fusion protein or peptide. In some cases, the expression vector may contain a promoter recognized by a host cell.

The promoter sequence may originate from a prokaryote, a eukaryote, or a virus. Examples of yeast-compatible promoters include GAPDH, PGK, ADH, PHO5, GAL1 and GAL10, but are not limited thereto.

The vector may have an additional expression control sequence. "Control sequences" refers to DNA sequences necessary for the expression of an operably linked coding sequence in a particular host organism. The control sequence may be a Shine-Dalgarno sequence. For example, the Shine-Dalgarno sequence can be from the replicase gene of phage MS-2 or from the cII gene of bacteriophage λ. Moreover, the vector may have an appropriate marker to screen the transformed host cell. The transformation of a host may be accomplished by any one of a variety of techniques well known in the art.

In still another exemplary embodiment, a recombinant microorganism comprising a microorganism transformed with a recombinant expression vector containing an isolated polynucleotide encoding yeast SNR84 is provided. The exemplary recombinant microorganism exhibits increased galactose catabolism due to the overexpression of SNR84.

The microorganism may be any microorganism capable of being transformed by the recombinant expression vector, for example, a bacteria, fungus or yeast.

In one embodiment, the microorganism is a yeast, examples of which include those selected from the group consisting of the genus *Saccharomyces*, the genus *Pachysolen*, the genus *Clavispora*, the genus *Kluyveromyces*, the genus *Debaryomyces*, the genus *Schwanniomyces*, the genus *Candida*, the genus *Pichia*, and the genus *Dekkera*, but are not limited thereto. In some embodiments, the yeast is *Saccharomyces cerevisiae* (*S. cerevisiae*) strain CEN.PK2-1D.

By overexpression of the SNR84 gene, the recombinant yeast strain rapidly converts galactose into a biofuel, for example ethanol, when cultured in a medium containing either a mixture of glucose and galactose, or only galactose as a carbon source. The overexpression of the SNR84 gene is involved in the improved cell growth observed when using galactose as a carbon source. An increase in galactose catabolism may lead to an improvement in the productivity of all biological processes when galactose is used as the primary carbon source.

The transformation of yeast is conducted using transformation methods which are known in the art and can be easily performed by a person of ordinary skill in the art. For example, the transformation of yeast using a recombinant expression vector may be conducted by the method described by Ito, Fukuoka, Murata, and Kimura ((1983) Transformation of Intact Yeast Cells Treated With Alkali Cations, *J. Bacteriol.* 153, 163-168).

In some embodiments in order to transform *S. cerevisiae* CEN.PK2-1D with a vector containing a heterogeneous gene, a spheroplast transformation kit (Bio 101, Vista, Calif.) is used. In such an embodiment, the transformed strain may be cultured in yeast synthetic complete (YSC) medium containing 20 g/l of glucose, and then continuously cultured in YSC medium containing 4% galactose. Afterward, strains with an improved galactose utilization rate may be screened on 4% galactose-containing YSC solid medium.

In one exemplary embodiment, a recombinant microorganism deposited with Accession No. KCTC 11388 BP is provided. The recombinant microorganism was deposited under the name of *Saccharomyces cerevisiae* strain CEN.PK2-1D/pRS424-SNR84 on Sep. 4, 2008 to the Korean Collection for Type Cultures (KCTC) at the Gene bank of the Korea Research Institute of Bioscience and Biotechnology (Yuseung-gu, Daejeon, Korea) with Accession No. KCTC 11388 BP. The deposited recombinant microorganism was identified by the methods described above as a yeast strain having excellent galactose availability.

2. Method of Producing Biofuel

In another exemplary embodiment, a method of producing biofuel from a galactose-containing carbon source is provided. The method comprises culturing a recombinant microorganism overexpressing a gene that improves galactose catabolism in a medium comprising galactose as a carbon source such that fermentation results in biofuel production. In some embodiments, the recombinant microorganism overexpresses an isolated polynucleotide encoding yeast SNR84. The recombinant microorganism can be a yeast strain.

As described herein, when the SNR84 gene is overexpressed, the volumetric productivity of biofuels, such as bioalcohols, may be increased. Without being bound by theory, the overexpression of the SNR84 gene induces the expression of the galactose-catabolizing gene(s), and thus galactose is rapidly converted to biofuel from the galactose-containing carbon source.

Examples of biofuels which may be produced include bioalcohols, such as ethanol, propanol or butanol; or acetone, but are not limited to these examples.

The galactose-containing carbon source contains either a mixture of galactose and glucose, or only galactose. The mixed ratio of the galactose to glucose in the medium is not limited. Specifically, the medium contains at least 40% galactose, or more specifically at least 50% galactose.

An experiment conducted by the present inventors shows that, in a medium containing galactose as a carbon source, the volumetric productivity of bioalcohol is greatly increased by using a yeast strain in which the SNR84 gene is overexpressed, as compared to the yeast strain which does not overexpress SNR84.

The galactose-containing carbon source may be a hydrolysate of algae biomass.

The type of algae from which the hydrolysate is obtained is not particularly limited and may include red algae (e.g., *Porphyra yezoensis* Ueda), brown algae (e.g., the Laminariaceae family, *Undaria pinnatifida* and *Hizikia fusiforme*), and green algae (e.g., *Enteromorpha* genus), for example.

Examples of red algae include *Gelidium amansii, Gracilaria verrucosa, Bangia atropurpurea, Porphyra suborbiculata, Porphyra yezoensis, Galaxaura falcate, Scinaia japonica, Gelidium divaricatum, Gelidium pacificum, Lithophylum okamurae, Lithothammion cystocarpideum, Amphiroa anceps, Amphiroa beauvoisii, Corallina officinalis, Corallina pilulifera, Marginisporum aberrans, Carpopeltis prolifera, Grateloupia filicina, Grateloupia elliptica, Grateloupia lanceolanta, Grateloupia turtuturu, Phacelocarpus japonicus, Gloiopeltis furcata, Hypnea charoides, Hypnea japonitca, Hypnea saidana, Chondrus cripspus, Chondracanthus tenellus, Gracilaria textorii, Lomentaria catenata, Heterosiphonia japonica, Chondria crassicaulis, Symphyocladia latiuscula*, but are not limited thereto. Further, a combination of algae comprising at least one of the foregoing can be used.

A method of producing ethanol from algae biomass may be conducted by any method known in the art. For example, ethanol may be produced from red algae biomass by direct saccharification which the red algae are directly saccharified, or by indirect saccharificationin which agar or cellulose is extracted from the red algae and then saccharified to obtain galactose or glucose. The saccharification may be performed by enzyme hydrolysis using galactocidase, or acid hydrolysis using a catalyst for acid hydrolysis. Then, ethanol may be produced by fermentation using any microorganism.

When biofuels are produced using algae biomass which is abundant in nature, resource supply and demand is stable. Thus, very high production efficiency of biofuels may be obtained.

3. Method of Screening Genes

In yet another exemplary embodiment, a method of screening yeast for genes in which galactose catabolism is increased when the genes are overexpressed is provided. The method comprises the following processes:

constructing a yeast genomic DNA library using a trp promoter-containing multi-copy plasmid; transforming a yeast with the constructed genomic DNA library to prepare a library of transformed yeast in which all yeast genes are overexpressed; culturing the transformed yeast library in a medium containing only galactose as a carbon source, and screening the transformed yeast for colonies having increased galactose availability, wherein the screening includes identifying fast-growing colonies of yeast (e.g. big colonies) through serial subculture; isolating the plasmid from the screened transformed yeast; and identifying the yeast genomic sequence inserted in the isolated plasmid.

FIG. 1 shows an exemplary method of screening genes for increased galactose catabolism. The gene screening method will be described in detail with reference to FIG. 1.

The yeast strain may be S. cerevisiae CEN.PK2-1D, and the multi-copy plasmid may be pRS424.

In any example, the yeast genomic DNA library may be prepared by cutting S. cerevisiae CEN.PK2-1D genomic DNA with a restriction enzyme, inserting the cut DNA fragment into the multi-copy plasmid (pRS424), and amplifying the recombinant plasmid in E. coli.

In constructing a transformed yeast library, the yeast transformation may be conducted using the method described by Ito., Fukuoka, Murata, and Kimura (J. bacteriol. (1983) 153, 163-168).

Then, the transformed yeast are screened for colonies exhibiting increased galactose availability (catabolism). Such colonies exhibit faster growth as evidenced by the formation of big colonies by serial subculture. Afterward, the plasmid is isolated from the screened transformed yeast, and the inserted yeast genomic sequence of the plasmid is identified. Here, the yeast genomic sequence may be analyzed using a gel documentation (gel doc).

In an embodiment, the gene screening method may further include: detecting the location of the inserted gene on the yeast genome by comparing the base sequence of the yeast genome with a predetermined length of genomic sequence present at each end of the gene inserted into the plasmid to identify the overexpressed gene; or re-transforming a yeast with the plasmid containing the identified gene to confirm an increase in galactose catabolism is caused by overexpression of the gene.

Accordingly, it can be confirmed that the gene identified by screening is a target yeast gene, and that the increase in galactose catabolism is caused by overexpression of the screened-gene.

In one exemplary embodiment, a gene for increasing galactose catabolism when overexpressed is provided, wherein said gene is screened by the above screening method.

The gene for increasing galatose catabolism is SNR84. The SNR84 gene may be encoded by the polynucleotide sequence set forth in SEQ ID NO: 1

The inventive concept will be described below with reference to the following examples.

EXAMPLE 1

Screening of Genes for Increased Galactose Catabolism When Overexpressed

Figure 2:
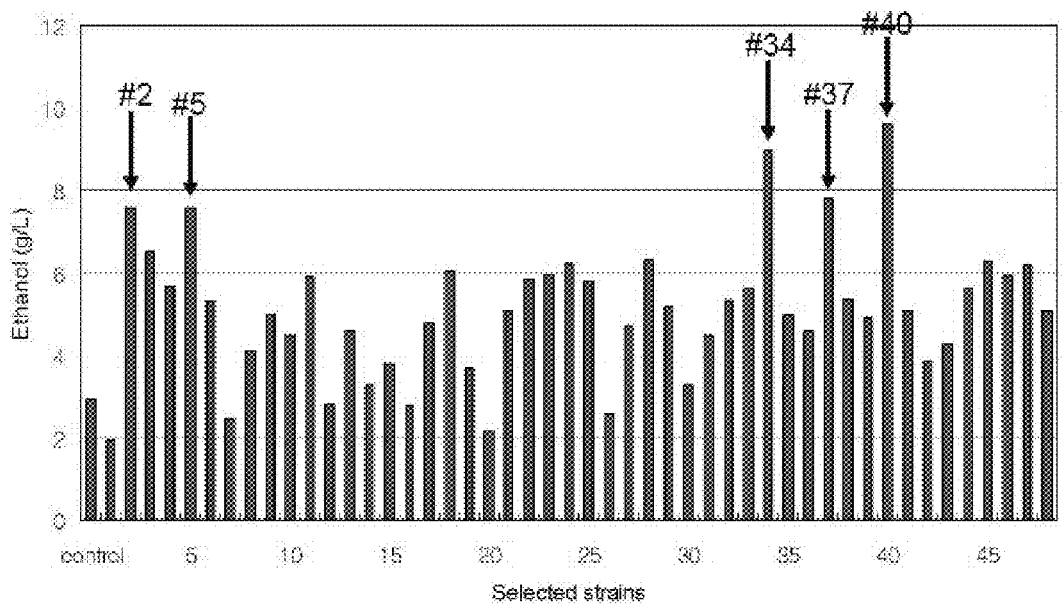
FIG. 2 is a graph showing ethanol productivity of various yeast strains, identified using the screening method of FIG. 1, in 5 ml yeast synthetic complete (YSC) medium containing 4% galactose for 20 h.
Figure 3:
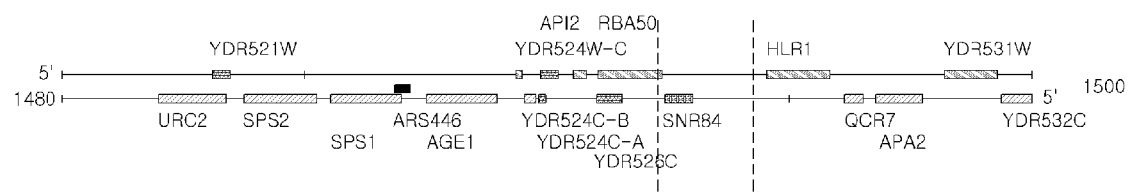
FIG. 3 is an enlarged genetic map of nucleotides 1492241~1494948 of yeast chromosome IV containing the SNR84 gene.

A genomic DNA library of S. cerevisiae CEN.PK2-1D was prepared using the multi-copy plasmid pRS424. The genomic library was introduced into the yeast under control of the trp promoter, thereby constructing a transformed yeast DNA library in which all the yeast genes are overexpressed. Following transformation, the constructed transformed yeast library was cultured in YSC medium containing only galactose as a carbon source, from which transformed yeast cells having increased galactose availability are screened by serial subculture. The volumetric amount of ethanol (g/L) produced by selected yeast strains (colonies) was compared by culturing strains in 5 ml YSC containing 4% galactose for a period of 20 h. As shown in FIG. 2, strains #2, 5, 34, 37, and 40 produced increased amounts of ethanol as compared to other transformed strains. The plasmid was isolated from yeast strain #40, and the yeast genomic sequence inserted in the isolated plasmid was determined using the known genomic sequence information located at both sides of the restriction enzyme site used in cloning the sequence. Then, the location of the insert genein the yeast genome was determined by comparing the yeast genome base sequence with a predetermined length of genomic sequence present at both ends of the insert gene to thereby identify the overexpressed yeast gene. As a result, it was determined that the genomic sequence introduced to the #40 yeast strain was, as shown in FIG. 3, a sequence consisting of 1492241 to 1494948 bases of the fourth chromosome of the yeast, including the genomic sequence of the SNR84 gene. Then, in order to confirm that the SNR84 gene was involved in increased galactose catabolism, yeast was transformed with a plasmid containing the isolated SNR84 gene, and it was confirmed that the increase in galactose catabolism was caused by the overexpression of the gene.

EXAMPLE 2

Evaluation of Galactose Catabolism

Figure 5:
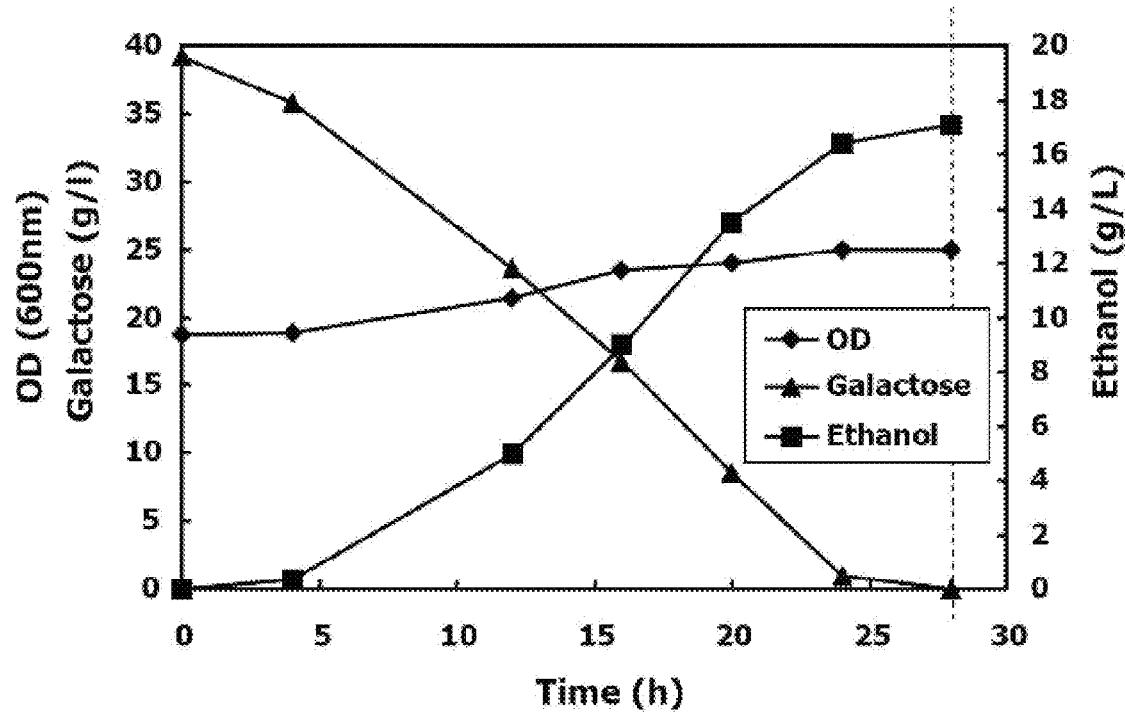
FIG. 5 is a graph showing galactose fermentation and ethanol production by wild type S. cerevisiae strain CEN.PK2-1D in 4% galactose-containing medium.
Figure 6:
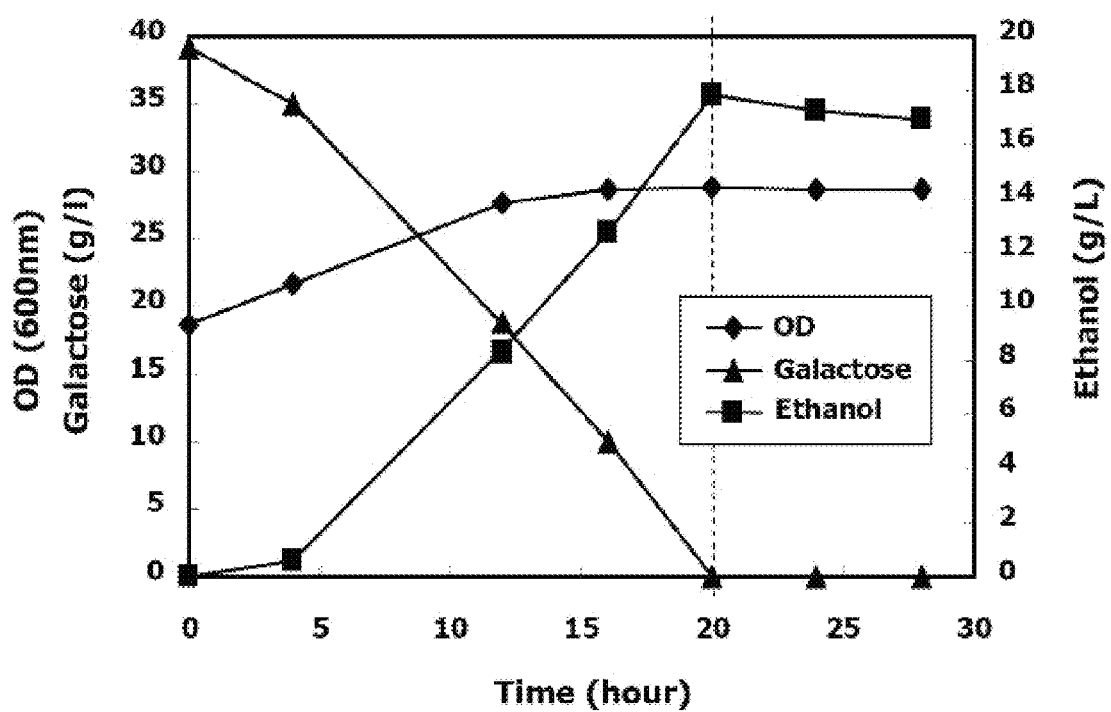
FIG. 6 is a graph showing an increase in galactose fermentation and ethanol production in a 4% galactose-containing medium by S. cerevisiae strain CEN.PK2-1D transformed with a multi-copy plasmid containing bases 1492241 to 1494948 of Chromosome IV, and including the SNR84 gene.

The S. cerevisiae CEN.PK2-1D (MATalpha; ura3-52; trp1-289; leu2-3_112; his3 D1; MAL2-8C; SUC2) strain was transformed with a multi-copy plasmid containing the DNA sequence corresponding to bases 1492241 to 1494948 of the fourth chromosome thereof, including the SNR84 gene, and cultured in a minimal medium containing 4% galactose for 20 hours. Then, the volumetric productivity of ethanol was determined to evaluate galactose catabolism. The results are shown in FIGS. 5 and 6, and Table 1.

TABLE 1

|  | wild type | snr84 |
| --- | --- | --- |
| Galactose consumption time | 28 h | 20 h |
| Ethanol concentration | 17 g/l | 18 g/l |
| Ethanol volumetric productivity | 0.61 g/lh | 0.9 g/lh |

The control strain (wild type) took 28 hours to completely consume the given amount of galactose, and then produced 17 g/L of ethanol. After 20 hours, the control strain produced 14 g/L of ethanol and left 8 g/L of galactose. In contrast, the snr84-overexpressed strain completely consumed galactose within 20 hours, and produced 18 g/L of ethanol.

This confirms that the snr84-overexpressing strain catabolized galactose much faster and produced more ethanol than the control strain. Thus, the volumetric productivity of ethanol was increased by 48% in the SNR84-overexpressed strain (snr84) as compared to the control strain.

The terminology used herein is for the purpose of describing particular embodiments only and is not intended to be limiting of the invention. The terms "a" and "an" do not denote a limitation of quantity, but rather denote the presence of at least one of the referenced item. The term "or" means "and/or". The terms "comprising", "having", "including", and "containing" are to be construed as open-ended terms (i.e. meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

While exemplary embodiments have been disclosed herein, it should be understood that various modifications or changes to the exemplary embodiments may be possible. Such modifications or changes are not to be regarded as a departure from the spirit and scope of the present application, and all such modifications as would be obvious to one skilled in the art are intended to be included within the scope of the following claims. Moreover, any combination of the above-described elements in all possible variations thereof is encompassed by the invention unless otherwise indicated herein or otherwise clearly contradicted by context.

What is claimed is:

1. A recombinant *Saccharomyces cerevisiae* microorganism overexpressing yeast SNR84, wherein the recombinant microorganism comprises a multi-copy plasmid expressing yeast SNR84 and shows increased galactose catabolism as compared to a *Saccharomyces cerevisiae* microorganism that does not overexpress yeast SNR84.

2. The recombinant microorganism of claim 1, wherein the recombinant microorganism is *Saccharomyces cerevisiae* strain CEN.PK2-1D/pRS424-SNR84 deposited with Korean Collection for Type Cultures under Accession No. KCTC 11388 BP.

3. A method of producing ethanol from a galactose-containing carbon source using a recombinant microorganism, wherein the method comprises incubating the recombinant microorganism of claim 1 in a galactose-containing carbon source such that the recombinant microorganism produces ethanol.

4. The method of claim 3, wherein production of ethanol is increased by overexpression of yeast SNR84 in the recombinant microorganism.

5. The method of claim 3, wherein the galactose-containing carbon source consists of galactose, or a mixture of glucose and galactose.

6. The method of claim 3, wherein the galactose-containing carbon source contains greater than or equal to 4% of galactose.

7. The method of claim 3, wherein the galactose-containing carbon source is a hydrolysate of algae biomass.

8. A method of producing ethanol from a galactose-containing carbon source using a recombinant *Saccharomyces cerevisiae* yeast strain, wherein the method comprises:
    transforming a *Saccharomyces cerevisiae* yeast with a recombinant vector comprising an isolated polynucleotide encoding yeast SNR84;
    culturing the recombinant *Saccharomyces cerevisiae* yeast strain in the galactose-containing carbon source, wherein the galactose-containing carbon source consists of galactose, or a mixture of glucose and galactose; and
    overexpressing yeast SNR84 in the recombinant *Saccharomyces cerevisiae* yeast strain,
    such that the recombinant yeast strain produces ethanol.

9. The method of claim 8, wherein the recombinant yeast strain is *Saccharomyces cerevisiae* strain CEN.PK2-1D/pRS424-SNR84 deposited with the Korean Collection for Type Cultures under Accession No. KCTC 11388 BP.

* * * * *